United States Patent [19]

Cheng

[11] Patent Number: 5,512,462
[45] Date of Patent: Apr. 30, 1996

[54] METHODS AND REAGENTS FOR THE POLYMERASE CHAIN REACTION AMPLIFICATION OF LONG DNA SEQUENCES

[75] Inventor: Suzanne Cheng, El Cerrito, Calif.

[73] Assignee: Hoffmann-La Roche Inc., Nutley, N.J.

[21] Appl. No.: 203,198

[22] Filed: Feb. 25, 1994

[51] Int. Cl.$^6$ .............................. C12P 19/34; C12N 9/00; C12N 9/12
[52] U.S. Cl. ................... 435/91.2; 435/183; 435/194
[58] Field of Search ................... 435/91.2, 183, 435/194

[56] References Cited

U.S. PATENT DOCUMENTS

| | | | |
|---|---|---|---|
| 5,198,543 | 3/1993 | Blanco et al. | 435/194 |
| 5,210,036 | 5/1993 | Comb et al. | 435/194 |
| 5,270,163 | 12/1993 | Gold et al. | 435/6 |
| 5,436,149 | 7/1995 | Barnes | 435/194 |

FOREIGN PATENT DOCUMENTS 9203556  3/1992  WIPO.

OTHER PUBLICATIONS

Perrino and Loeb, 1990, "Hydrolysis of 3'-Terminal Mispairs in Vitro by the 3'-5' Exonuclease of DNA Polymerase Delta Permits Subsequent Extension by DNA Polymerase Alpha" Biochemistry 29:5226–5231.
Rychlik et al., 1990, "Optimization of the Annealing Temperature for DNA Amplification in Vitro" Nucleic Acids Research 18(21):6409–6412.
Eckert and Kunkel, 1991, in PCR: A Practical Approach eds. McPherson et al., IRL Press at Oxford University Press, Oxford "The Fidelity of DNA Polymerases Used in the Polymerase Chain Reactions".
Glukhv et al., 1991, "PCR Amplification of Phage Lambda DNA Sequences Using Thermostable DNA Polymerase" Molekulyarnaya Biologiya 25(6):1602–1610.
Krishnan et al., 1991, "Direct and Crossover PCR Amplificiation to Facilitate Tn5supF-based Sequencing of Lambda Phage Clones" Nucleic Acids Research 19(22):6177–6182.
Ling et al., 1991, "Optimization of the Polymerase Chain Reaction With Regard to Fidelity: Modified T7, Taq, and Vent DNA Polymerases" PCR Methods and Applications 1:63–69.
Maga and Reichardson, 1991, "Amplification of 9.0 kb Fragment Using PCR" BioTechniques 11(2):185–186.
Pomp and Medrano, 1991, "Organic Solvents as Facilitators of Polymerase Chain Reaction" BioTechniques 10(1):58–59.
Wong et al., 1991, "Branch Capture Reactions: Displacers Derived From Asymmetric PCR" Nucleic Acids Research 19(9):2251–2259.
Filichkin and Gelvin, 1992, "Effect of Dimethyl Sulfoxide Concentration on Specificity of Primer Matching in PCR" BioTechniques 12(6):828–830.
Kainz et al., 1992, "In Vitro Amplification of DNA Fragments >10 kb" Analytical Biochemistry 202:46–49.
Korge et al., Feb., 1992, "Extensive Size Polymorphism of the Human Keratin 10 Chain Resides in the C-Terminal V2 Subdomain Due to Variable Numbers and Sizes of Glycine Loops" Proc. Natl. Acad. Sci. USA 89:910–914.
Ohler and Rose, 1992, "Optimization of Long–Distance PCR Using a Transposon-Based Model System" PCR Methods and Applications 2:51–59.
Ponce and Micol, 1992, "PCR Amplification of Long DNA Fragments" Nucleic Acids Research 20(3):623.
Yen et al., March, 1992, "Age-Dependent 6KB Deletion in Human Liver Mitochondrial DNA" Biochemistry International 26(3):457–468.
Shen and Hohn, Jul., 1992, "DMSO Improves PCR Amplification of DNA With Complex Secondary Structure" Trends in Genetics 8(7):227.
Chester et al., 1993, "Dimethyl Sulfoxide–Mediated Primer Tm Reduction: A Method for Analyzing the Role of Renaturation Temperature in the Polymerase Chain Reaction" Analytical Biochemistry 209:284–290.
Ohler et al., 1993, "Use of a Sensitive Fluorescent Intercalating Dye to Detect PCR Products of Low Copy Number and High Molecular Weight" PCR Methods and Applications 3:115–119.
Perkin Elmer Guide to PCR Enzymes, Jun., 1993, pp. 9–11 "Recombinant Thermus thermophilus (rTth) DNA Polymerase" and UlTma DNA Polymerase.
New England Biolabs 1993/1994 Catalog pp. 62 and 63.
Good and Izawa, 1972, "Hydrogen Ion Buffers" Methods in Enzymology 24(Part B):53–68.
Griep and McHenry, 1989, "Glutamate Overcomes the Salt Inhibition of DNA Polymerase III Holoenzyme" J. Biological Chemistry 264(19):11294–11301.
Perrino and Loeb, Feb., 1989, "Differential Extension of 3' Mispairs is a Major Contribution to the High Fidelity of Calf Thymus DNA Polymerase-alpha" J. Biological Chemistry 264(5):2898–2905.
Perrino and Loeb, May, 1989, "Proofreading by the E Subunit of *Escherichia coli* DNA Polymerase III Increases the Fidelity of Calf Thymus DNA Polymerase Alpha" Proc. Natl. Acad. Sci. USA 86:3085–3088.

*Primary Examiner*—W. Gary Jones
*Assistant Examiner*—Dianne Rees
*Attorney, Agent, or Firm*—George M. Gould; Dennis P. Tramaloni; Douglas A. Petry

[57] ABSTRACT

Methods and reagents are provided for the amplification of DNA sequences longer than 10 kilobases by the polymerase chain reaction (PCR). The methods use compositions consisting of a primary thermostable DNA polymerase from *Thermus thermophilus* combined with a lesser amount of a secondary thermostable DNA polymerase possessing a 3'-to-5' exonuclease activity from *Thermococcus litoralis*, Pyrococcus species GB-D or *Thermotoga maritima*. The DNA polymerase compositions, when used with the disclosed reaction buffer, enable amplifications of DNA sequences up to at least 42.2 kilobases in length.

6 Claims, No Drawings

METHODS AND REAGENTS FOR THE POLYMERASE CHAIN REACTION AMPLIFICATION OF LONG DNA SEQUENCES

BACKGROUND OF THE INVENTION

1. Field of the Invention

The present invention relates generally to the fields of molecular biology and nucleic acid chemistry. More specifically, it relates to methods for the polymerase chain reaction amplification of long nucleic acid sequences.

2. Description of Related Art

The polymerase chain reaction (PCR), a powerful tool for the amplification of nucleic acid sequences, is disclosed in U.S. Pat. Nos. 4,683,202; 4,683,195; 4,800,159; and 4,965,188, each incorporated herein by reference. In its simplest form, PCR is an in vitro method for the enzymatic synthesis of specific DNA sequences, using two oligonucleotide primers that hybridize to complementary strands and flank the region of interest in the target DNA. A repetitive series of reaction steps involving template denaturation, primer annealing, and the extension of the annealed primers by a DNA polymerase results in the geometric accumulation of a specific fragment whose termini are defined by the 5' ends of the primers. PCR is capable of producing a selective enrichment of a specific DNA sequence by a factor of $10^9$. The PCR method is also described in Saiki et al., 1985, *Science* 230:1350, incorporated herein by reference.

PCR has been widely applied in molecular biology, molecular evolution, medical genetics, population genetics, forensic biology, and genome mapping and sequencing projects. However, current PCR are limited in the size of the region of DNA that can be amplified reliably.

Attempts to overcome the length limitations of PCR are reported in Glukhov et al., 1991, *Molek. Biol.* 25:1602–1610; Kainz et al., 1992, *Anal. Biochem.* 202:46–49; Ohler and Rose, 1992, *PCR Meth. Applic.* 2:51–59; Ponce and Micol, 1992, *Nucl. Acids Res.* 20:623; and Rychlik et al., 1990, *Nucl. Acids Res.* 18:6409–6412; each incorporated herein by reference. Although amplifications of 5–15 kb sequences were achieved, the reported yields of the longer products were low.

PCR methods capable of amplifying long nucleic acid sequences would facilitate genomic mapping and sequencing as well as molecular cloning through the amplification of long, low-copy insert material, and by making possible the assembly of larger recombinant constructions in PCR-based mutagenesis. There remains a need for methods that will enable PCR amplification of targets of at least 25 kb with high yields.

SUMMARY OF THE INVENTION

The present invention provides improved methods and reagents for the PCR amplification of long DNA targets.

One aspect of the invention relates to combinations of thermostable DNA polymerases which are useful in the methods of the present invention. The combinations consist primarily of *Thermus thermophilus* DNA polymerase, a highly active thermostable DNA polymerase that does not exhibit 3'-to-5' exonuclease activity, and secondarily of either *Thermococcus litoralis*, Pyrococcus species GB-D, or *Thermotoga maritima* DNA polymerase, all thermostable DNA polymerases that exhibit 3'-to-5' exonuclease activity.

Another aspect of the invention relates to a buffer useful for carrying out the amplification of long targets.

Another aspect of the present invention relates to PCR amplifications using the specific combinations of thermostable enzymes described above. The reaction conditions are specified so as to enable the amplification of nucleic acid target sequences of up to 42 kilobases in length.

Another aspect of the invention relates to kits comprising reagents useful in carrying out the methods of the present invention. Such kits comprise a combination of thermostable DNA polymerases as described above and, optionally, additional amplification reagents which are useful in the methods of the present invention.

DETAILED DESCRIPTION OF THE INVENTION

To aid in understanding the invention, several terms are defined below.

The term "amplification reaction mixture", as used herein, refers to an aqueous solution comprising the various amplification reagents used to amplify a target nucleic acid. The reagents include primers, enzymes, aqueous buffers, salts, target nucleic acid, and deoxynucleoside triphosphates (both conventional and unconventional). Depending on the context, the mixture can be either a complete or incomplete reaction mixture.

The terms "nucleic acid" and "oligonucleotide", as used herein, refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid" and "oligonucleotide", and these terms will be used interchangeably. These terms refer only to the primary structure of the molecule. Thus, these terms include double- and single-stranded DNA, as well as double- and single-stranded RNA.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "hybridization", as used herein, refers to the formation of a duplex structure by two single stranded nucleic acids due to complementary base pairing. Hybridization can occur between complementary nucleic acid strands or between nucleic acid strands that contain minor regions of mismatch. Stability of a nucleic acid duplex is measured by the melting temperature, or "$T_m$." The $T_m$ is the temperature (under defined ionic strength and pH) at which 50% of the base pairs have dissociated. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Conditions under which only fully complementary nucleic acid strands will hybridize are referred to as "stringent hybridization conditions". Stringent hybridization conditions are well known in the art (see, e.g., Sambrook et al., 1985, *Molecular Cloning—A Laboratory Manual*, Cold Spring Harbor Laboratory, Cold Spring Harbor, New York, incorporated herein by reference). Generally, stringent conditions are selected to be about 5° C. lower than the $T_m$ for the specific sequence at a defined ionic strength and pH. Typically, stringent conditions will be those in which the salt concentration is at least about 0.2 molar at pH7 and the temperature is at least about 60° C. Relaxing the stringency of the hybridizing conditions will allow sequence mismatches to be tolerated; the degree of mismatch tolerated can be controlled by suitable adjustment of the hybridization conditions.

Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs.

The term "primer", as used heroin, refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template.

A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis. For example, non-complementary sequences can be located at the ends of the primer to provide restriction enzyme cleavage sites useful in the cloning of an amplified sequence.

The terms "upstream" and "downstream", as used herein, refer to the location of the primer binding sites along the target sequence. The upstream primer hybridizes to the non-coding strand of the target sequence, and therefore forms the 5' end of the amplified sequence which is a subsequence of the coding strand of the target sequence. Similarly, the downstream primer hybridizes to the coding strand of the target sequence, and therefore forms the 5' end of the amplified sequence which is a subsequence of the non-coding strand of the target sequence.

The terms "target sequence" and "target nucleic acid sequence", as used herein, refer to a region of the oligonucleotide which is to be amplified, detected, or both. The target sequence resides between the two primer sequences used for amplification.

The term "thermostable nucleic acid polymerase", as used herein, refers to an enzyme which is relatively stable to heat when compared, for example, to nucleotide polymerases from *E. coli*, and which catalyzes the polymerization of nucleoside triphosphates. Generally, the enzyme will initiate synthesis at the 3'-end of the primer annealed to the target sequence, and will proceed in the 5'-direction along the template until synthesis terminates.

The methods of the present invention use specific combinations of a DNA polymerase from *Thermus thermophilus* (Tth) with a DNA polymerase from either *Thermotoga maritima* (Tma), Pyrococcus species GB-D, or *Thermococcus litoralis* (Tli).

The terms "3'-to 540 nuclease activity" and "proofreading activity", as used herein, refer to that activity of a template-specific nucleic acid polymerase whereby nucleotides are removed from the 3' end of an oligonucleotide in a sequential manner.

A unit (U) of polymerase activity is a measure of the amount of enzyme needed to synthesize nucleic acid at a given rate. The activity units specified herein are as defined by the respective suppliers of each polymerase, as listed below. Because activities may be assayed under different specific conditions, activity of one enzyme may not be directly comparable to activity of another enzyme.

Recombinant DNA polymerases from *Thermus thermophilus* (rTth) and *Thermatoga maritima* (UlTma) are commercially available from Perkin Elmer, Norwalk, Conn. One unit of rTth or UlTma™ DNA polymerase is defined by the commercial supplier, Perkin Elmer, as the amount of enzyme that will incorporate 10 nmoles of dNTP into acid insoluble material at 74° C. in 30 minutes, as measured in a 10 minute incubation in a 50 μl reaction consisting of the following:

200 μM each dATP, dGTP, dTTP

100 μM [α-$^{32}$P]-dCTP (0.05 to 0.1 Ci/mmole) activated salmon sperm DNA 100 mM KCl 2.2 mM MgCl$_2$ 25 mM TAPS [tris-(hydroxymethyl)-methyl-amino-propanesulfonic acid, sodium salt], pH 9.3 at 25° C.

1 mM beta-mercaptoethanol

Recombinant DNA polymerases from *Thermococcus litoralis* (Vent$_R$®) and Pyrococcus species GB-D (Deep Vent$_R$®) are commercially available from New England Biolabs, Beverly, Mass. One unit of Vents$_R$® or Deep Vent$_R$® DNA polymerase is defined by the commercial supplier, New England Biolabs, as the amount of enzyme that will incorporate 10 nmoles of dNTP into acid insoluble material at 75° C. in 30 minutes in a reaction consisting of following:

200 μM each dNTP (dATP, dCTP, dGTP, and $^3$H-dTTP)

0.2 mg/ml activated DNA 10 mM KCl 10 mM (NH$_4$)$_2$SO$_4$ 20 mM Tris-HCl, pH 8.8 at 25° C.

2 mM MgSO$_4$ 0.1% Triton X-100

Conventional techniques of molecular biology, microbiology and recombinant DNA techniques, which are within the skill of the art, are explained fully in the literature. See, e.g., Sambrook, Fritsch and Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, ed., 1984); *A Practical Guide to Molecular Cloning* (B. Perbal, 1984); and a series, *Methods in Enzymology* (Academic Press, Inc.); each incorporated heroin by reference.

The present invention provides improved methods and reagents for the PCR amplification of long DNA targets. The PCR amplification process for the amplification of short nucleic acid sequences is well known in the art and described in U.S. Pat. Nos. 4,683,195; 4,683,202; and 4,965,188, each incorporated herein by reference. Commercial vendors, such as Perkin Elmer, Norwalk, Conn., market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

In order to achieve efficient PCR amplification of long targets, several requirements must be met. First, target sequences must be completely denatured. Longer targets are increasingly likely to contain GC-rich stretches that are prone to incomplete denaturation because of their relatively high melting temperatures. Incomplete strand separation permits rapid renaturation of the target DNA, possibly precluding the annealing and extension of PCR primers. Second, extension times must be sufficiently long to allow the completion of strand synthesis in each PCR cycle. Third, long targets must be protected against degradation during amplification. Long targets are more susceptible to degradation and strand breakage under PCR conditions. Initial template integrity and subsequent strand survival during PCR are therefore important considerations. The methods of the present invention are designed to meet these requirements for long PCR without compromising either polymerase activity or the specificity necessary for single-copy gene amplifications from genomic DNA.

Improving target strand separation, lengthening the extension times, and protecting the template DNA from degradation during thermal cycling greatly increase the maximum amplifiable target length, but are insufficient to achieve efficient amplification of targets in the 23–42 kb range. The fidelity of nucleic acid synthesis is a limiting factor in achieving amplification of long target molecules.

The misincorporation of nucleotides during the synthesis of primer extension products limits the length of target that can be efficiently amplified. The effect on primer extension of a 3'-terminal base that is mismatched with the template is described in Huang et al., 1992, *Nucl. Acids Res.* 20:4567–4573, incorporated herein by reference. The presence of misincorporated nucleotides may result in prematurely terminated strand synthesis, reducing the number of template strands for future rounds of amplification, and thus reducing the efficiency of long target amplification. Even low levels of nucleotide misincorporation may become critical for sequences longer than 10 kb.

The fidelity of DNA synthesis is improved if a small amount of thermostable 3'-to5' exonuclease, or "proofreading", activity is present in the reaction in addition to the DNA polymerase activity. The proofreading activity apparently improves the yields of long products by removing misincorporated nucleotides and permitting complete strand synthesis by the predominant polymerase activity. An important aspect of the present invention refers to specific mixtures of thermostable DNA polymerases that greatly increase the maximum target length amplifiable by providing both 3'-to-5' exonuclease activity and polymerase activity.

Proofreading exonuclease activity is not found in Tth DNA polymerase (Myers and Gelfand, 1991, *Biochemistry* 3:766 1–7666, incorporated herein by reference), but is inherent in the DNA polymerases from *Thermococcus litoralis*, Pyrococcus species GB-D, and *Thermatoga maritima*. However, amplification of long targets with Vent$_R$® DNA polymerases alone is less efficient than with Tth DNA polymerase which does not exhibit 3'-to-5' exonuclease activity. The decreased amplification efficiency is probably due, at least in part, to primer degradation and a decrease in net processivity resulting from the competition between the 3'-to 5' exonuclease and polymerase activities.

The relative amounts of 3'-to-5' exonuclease activity and polymerase activity can be controlled by mixing DNA polymerases. By combining a small amount of a secondary polymerase which has proofreading activity, such as Tli DNA polymerase, with an active primary polymerase, such as Tth DNA polymerase, the advantage of a proofreading activity can be combined with the active DNA polymerase activity inherent in the primary polymerase.

Nearly all aspects of PCR protocols affect the amplification efficiency of long target molecules. Extension times, cosolvents, and polymerases (with and without 3'- to-5'-exonuclease activity) are the most critical parameters, but the pH and composition of the reaction buffer, salts (K+and Mg$^{2+}$), and primer design are also important variables for the success of amplifications of long targets. The effects of the individual components of a PCR amplification on the amplification efficiency of long targets are discussed below.

Temperature Cycling

The amplification reactions exemplified herein use a two-step temperature cycle in which the reaction temperature alternates between a high temperature at which the target nucleic acid is denatured, and a lower temperature at which the primers anneal to the denatured target sequences and primer extension occurs. The time and temperature of each step in each cycle effects the efficiency of amplification.

More complete target denaturation can be achieved by raising the denaturation temperature. However, raising the denaturation temperature may cause higher rates of damage, such as depurination, which decreases the amplification efficiency, as well as increases loss of polymerase activity. Although it is important to achieve complete denaturation of the target nucleic acid, the rate of target damage must be simultaneously minimized. Consequently, moderate denaturation temperatures (e.g., 94° C., depending on GC content) are preferred, with the completeness of denaturation improved by the addition of cosolvents, as described below.

A relatively high annealing temperature (e.g., 68° C.) reduces the hybridization of primers to partially homologous target sites, thereby minimizing the synthesis of products from secondary priming sites. In amplifications using lambda DNA target as described in the Examples, a minimum of 5–6 minutes at 68° C. is needed. The addition of a more stringent 70°–75° C. annealing step does not significantly improve yields. Similarly, more complex temperature profiles with temperature spikes to accommodate potentially problematic GC- or AT-rich stretches are not significantly beneficial.

An extension time that permits the completion of strand synthesis is critical for achieving amplification of long targets. For the amplification of targets longer than 20 kb, an annealing and extension time of at least 12 minutes, but no more than 22 minutes in any cycle, is preferred. Minimum extension times are dependent upon other factors, such as cosolvent levels, as discussed below. Amplification reactions in which the initial extension time used is about 12 minutes and the extension time is increased 15–20 seconds per cycle yield less non-specific product formation than reactions in which an extension time of more than 15 minutes is used throughout the amplification. The autoextension feature of the thermal cycler marketed by Perkin Elmer, Norwalk, Conn., provides a convenient way to increase the extension times during an amplification reaction.

Reducing Amplification Non-specific Targets

Typically, PCR reagents are combined at room temperature before the initial denaturation step. The low, less stringent temperature can result in the binding of primers either to other primers or to partially-homologous target sequences. Extension products can be formed from this non-specific primer binding which can lead to short products that serve as extremely efficient target competitors, thereby reducing the efficiency of amplification of the desired long product. A "hot-start" method minimizes the synthesis of primer extension product from non-specific primer hybridizations by inhibiting extension reactions until the reaction temperature is increased enough to prevent such non-specific binding. Since genomic templates are likely to contain sequences of partial homology to the target primer sequences, a hot-start protocol is important to maximize efficiency of long target amplification.

One method of achieving a hot-start involves withholding an essential PCR reaction component until the temperature of the amplification mixture has been raised to 75°–80° C. Examples include withholding either the DNA polymerase or $Mg^{2+}$, which is an essential catalyst for DNA polymerase activity. In one hot-start protocol, the essential component is added by hand after the denaturation temperature has been reached. Alternatively, the essential reaction component can be withheld by separating reaction components within a reaction tube using a heat-labile barrier, such as a wax that melts at the reaction temperatures. This minimizes the number of times the reaction tube must be opened, thereby decreasing the possibility of contamination.

Another hot-start protocol which may be useful in the methods of the present invention utilizes uracil-N-glycosylase to degrade any non-specific product formed before the amplification mixture temperature is raised (see co-pending U.S. Ser. No. 07/960,362, filed Jan. 5, 1993, which is incorporated herein by reference).

PCR Reagents

In a PCR, the primer extension reaction occurs when the primer-template mixture is incubated with a DNA polymerase under suitable polymerization conditions. These conditions are provided by a reaction mixture containing a divalent cation, a monovalent cation, all four deoxyribonucleotide triphosphates (dNTPs), and a buffering agent. Cosolvents may be added to the reaction mixture which affect the denaturation conditions. Each of these components affects the efficiency of the extension reaction and is discussed separately below.

DNA Polymerase

The choice of the combination of thermostable DNA polymerases and their concentrations becomes particularly important as the target length or sequence complexity is increased. The combination of Tth DNA polymerase and Tli DNA polymerase provides the most efficient amplification of long PCR products, and allows amplification of targets over 40 kb in length.

The optimal amount of DNA polymerase in a PCR amplification depends on a number of factors, including the number of copies of target sequences present in the sample. For high-copy reactions ($\geq 10^7$ copies of target), higher yields are obtained by using 2–2.5 units (U) Tth DNA polymerase per 50 μl reaction. Further increases in polymerase concentration result in an increase in the amplification of non-specific target molecules, resulting in higher background levels when the amplified products are detected by agarose gel electrophoresis. For low-copy reactions ($\leq 10^4$ copies of target), however, specificity is maximized using about 0.8–1 U Tth DNA polymerase per 50 μl reaction. For intermediate copy numbers of target, maximum yields are achieved using intermediate polymerase concentrations. The optimal polymerase concentration is also dependent on the divalent cation concentration. At higher $Mg^{2+}$ concentrations, polymerase levels were reduced to minimize accumulation of nonspecific products.

Using PCR with Tth DNA polymerase alone, the maximum target size amplifiable from high-copy phage lambda DNA samples was found to be limited to about 23 kb. Similarly, the maximum target size amplifiable from low-copy phage lambda DNA samples was found to be limited to about 10–12 kb. Dramatic increases in the size of the amplifiable target are achieved by adding a small amount of thermostable 3'-to-5'-exonuclease.

As described above, 3'-to-5' exonuclease activity is not found in Tth DNA polymerase. Proofreading activity is added by combining the Tth DNA polymerase with a small amount of thermostable DNA polymerase that has a proofreading activity, such as the DNA polymerases from *Thermococcus litoralis*, Pyrococcus species GB-D, and *Thermotoga maritima*. Low concentrations of any of these DNA polymerases are effective in extending the range of target sizes amplifiable by PCR using either Tth DNA polymerase; however, a combination of Tth and Tli DNA polymerases has been found to be the most reliable and efficient.

The optimal concentration ratio is approximately 0.015–0.15 U Tli DNA polymerase per 2–2.5 U Tth DNA polymerase for amplifications from high-copy samples ($\geq 10^7$ copies of target in a 50 μl reaction). For amplifications from low-copy samples ($\leq 10^4$ copies of target in a 50 μl reaction), the optimal concentration ratio is approximately 0.015–0.15 U Tli DNA polymerase per 0.8–1 U Tth DNA polymerase. Higher concentrations of Tli DNA polymerase reduce yield, possibly due to primer degradation.

Cosolvents

A cosolvent, such as glycerol, is a critical reaction component for the efficient amplification of long targets. A number of cosolvents have been reported to facilitate PCR, including glycerol, dimethylsulfoxide (DMSO), polyethylene glycol, and formamide. One way in which a cosolvent may influence the efficiency of long-target amplifications is by increasing the thermal stability of the DNA polymerase. Increasing the thermal stability slows the loss of DNA polymerase activity during the repeated high-temperature denaturation steps.

Another effect is that a cosolvent may effectively lower the melting and strand separation temperatures, thus facilitating the denaturation of the template and increasing the specificity of primer annealing. For example the melting temperature can be lowered by 2.5°–3° C. by the addition of 10% glycerol. Thus, by the addition of a cosolvent, an increase in the completeness of target denaturation can be achieved without raising the denaturation temperature, which would simultaneously increase the degradation of target molecules, as discussed above.

A standard Tth PCR buffer typically contains 5% (v/v) glycerol. An increase in the amount of glycerol added to an amplification reaction can significantly improve the amplification of long target sequences. Significant increases in the yield of a 9.4 kb target result from supplementing a standard Tth PCR buffer with 5% (w/v) glycerol. The percentages described here do not include any glycerol contribution from the various enzyme stocks used.

DMSO, preferably in a concentration of about 5–6% (v/v), may also be used alone. However, combinations of glycerol and DMSO are more effective for longer targets. Preferred concentration combinations include 5–14% (w/v) glycerol with 0.5–5% (v/v) DMSO. For example, amplifications of phage lambda targets 25–34 kb long were enhanced by the combination of 1–3% (v/v) DMSO with 10% glycerol, or by using 5% of both cosolvents; amplifications of phage lambda targets 35–42 kb long were most enhanced by the combination of 8–9% glycerol with 5% DMSO. Furthermore, with a combination of 3% DMSO and 10% glycerol, targets of up to 34 kb were readily amplified with a 10-minute extension time; with a combination of 1% DMSO and 10% glycerol, amplification was limited to 26 kb targets. A preferred combination consists of 10% glycerol and 2.25% DMSO.

DMSO, unlike glycerol, reduces the thermal stability of the polymerase. However, the effective lowering of melting and strand separation temperatures by 5.5°–°6° C. per 10% DMSO may be the dominant effect in long PCR. The addition of DMSO may also increase the DNA stability by decreasing the rates of depurination and/or chain scission and may accelerate strand renaturation. The reduction of melting and strand separation temperatures by combinations of glycerol and DMSO is generally consistent with a total reduction estimated by adding the effects of each component alone. The enhancement of yields resulting from the effective lowering of the melting and strand separation temperatures by the addition of a cosolvent, as discussed above, is not readily duplicated by raising the denaturation or annealing temperature during PCR.

Buffers

The pH of an amplification mixture affects the stability of the template DNA. Increasing the pH of the reaction can decrease the degradation of template DNA during thermal cycling. Although PCR amplification mixtures are pH buffered, the pH of a typical PCR reaction varies considerably during the temperature cycling because of the temperature dependence of the reaction buffer. The buffering agent used in a typical PCR is Tris, which has a $\Delta pKa$ of –0.031 per ° C. The fluctuation in pH during the temperature cycling can be decreased by using a buffering agent with a smaller $\Delta pKa$.

Two suitable buffers are Tris(hydroxymethyl)methylglycine (tricine), which has a $\Delta pKa$ of –0.021 per ° C., and N,N-Bis(hydroxyethyl)glycine (bicine), which has a $\Delta pKa$ of –0.018 per ° C.; both values measured at 20° C. and 0.1M ionic strength (see Good and Izawa, 1972, Meth. Enzymol. 24, Part B:53–68, incorporated herein by reference). With either a tricine or bicine buffer, the pH remains higher during the high temperature reaction conditions than with the typical Tris buffer, and the fluctuations in pH caused from the temperature cycling are decreased.

Optimal buffers and pH are dependent on, among other things, the DNA polymerase used. Using Tth DNA polymerase, a buffer consisting of 10–35 mM, preferably 20–25 mM, tricine at pH 8.5–8.7 (25° C.) provides the most reliable results. Optimal buffer conditions may need to be determined empirically for the amplification of specific targets.

Divalent Cation

The preferred divalent cation for the amplification of DNA is $Mg^{2+}$. In the absence of added 3'-to-5'-exonuclease activity, long PCR is enhanced at total $Mg^{2+}$ levels of 1.7–2 mM. In the presence of proofreading activity, however, the highest yields are obtained with 0.9–1.3 mM total $Mg^{2+}$. Increased yields of some targets can be achieved by increasing the $Mg^{2+}$ concentration up to 1.5 mM while reducing the total enzyme concentration, particularly the primary polymerase levels (to 1.25–2 U Tth DNA polymerase). However, for some targets, reducing total enzyme levels in order to reduce the synthesis of non-specific products at higher $Mg^{2+}$ levels also reduces product yields. As with K+ levels described below, the $Mg^{2+}$ optimum for each system may need to be determined empirically.

Monovalent Cation

The preferred monovalent cation is $K^+$, supplied as KOAc (K-acetate) or KCl. For the amplification of long target molecules, reduced $K^+$ levels are beneficial. A decrease in non-specific background can be achieved if the $K^+$ is supplied as KOAc rather than KCl. In general, $K^+$ concentrations reduced by 10–40% are more favorable to long PCR than the standard levels (100 mM KCl for use with Tth DNA polymerase). Preferred concentrations for use with Tth DNA polymerase are 60–100 mM KOAc, preferably 80–85 mM KOAc. Optimal concentration ranges may be system-dependent.

The efficiency of PCR amplifications using tricine or bicine buffers is similar using either KCl or KOAc as the monovalent cation. However, improved reaction robustness is realized using a tricine/KOAc buffer. A tricine/KOAc buffer has a slightly lower ionic strength than a tricine/KCl buffer, which could help destabilize secondary structures in a template with a high G+C content, thereby improving the completeness of target denaturation.

Although KCl and KOAc are the preferred monovalent salts, other monovalent salts may be useful in the methods of the present invention. These include NaCl, $(NH_4)_2SO_4$, K-glutamate, and $NH_4$-acetate.

Primers

Primer concentrations may need to be optimized for each system and approximate starting template copy number. For example, for the phage lambda amplification reactions described in the Examples, below, a higher concentration of primer was optimal for amplifying samples containing a high copy number of target than was optimal for amplifying samples containing a low copy number of target. For the high-copy reactions ($\geq 10^7$ copies of target), the optimum primer concentration was 0.4–0.5 μM of each primer. For low-copy amplifications ($\leq 10^4$ copies of target), 0.15–0.2 μM of each primer was most effective in the absence of proofreading activity, and 0.2 μM of each primer was best if 3'-to-5'-exonucleolytic activity was present. For intermediate copy-number reactions, increasing the primer concentration above 0.2 μM was as least as effective as increasing DNA polymerase levels, as discussed above, in enhancing yields. The improved PCR protocols that enable the amplification of target nucleic acid sequences up to 42 kb in length are summarized in Table 1, below.

TABLE 1

Optimal Long PCR Conditions

Temperature profile
    25 to 40 amplification cycles (template copy number dependent)
    Two-temperature cycling:
        (a) Short denaturation step, (e.g. 94° C. for 10–15 seconds)
        (b) Long annealing/extension step, (e.g. 68° C. for 10–14 minutes initially,
        increased by 15–20 seconds per cycle for at least 5–8 cycles)
    Final hold at 72° C. for at least 10 minutes
Hot-start
    Separate reagent ($Mg^{2+}$, enzyme, or dNTPs) until all samples have reached
    75–80° C., preferably using a wax barrier.
Primary polymerase
    2.5 units Tth DNA polymerase per 50 μl for high-copy template ($\geq 10^7$ copies)
    0.8–1.0 units Tth DNA polymerase per 50 μl for low-copy template ($\leq 10^4$ copies)
3'-to-5'-exonuclease (high- or low-copy template)
    0.015–0.15 units Tli DNA polymerase per 50 μl
Cosolvent
    5–14% glycerol with 0.5–5% DMSO
Buffer
    20–25 mM tricine or bicine, pH 8.5–8.7
Divalent cation
    0.9–1.5 mM $Mg^{2+}$ total; 0.2 mM changes can be critical
Monovalent cation
    80–85 mM KOAc
Primer design
    Either 20–23 bp with 50–60% GC content, or longer sequences, to permit the use
    of relatively high annealing temperatures.
Primer concentration
    0.4–0.5 μM for high-copy template ($\geq 10^7$ copies)
    0.15–0.2 μM for low-copy template ($\leq 10^4$ copies)
dNTP concentration
    0.2 mM each dATP, dCTP, dGTP, dTTP In general, the nucleic acid in the sample will be DNA, most usually genomic DNA. However, the present invention can also be practiced with other nucleic acids, such as RNA or cloned DNA, and the nucleic acid may be either single-stranded or double-stranded in the sample and still be suitable for purposes of the present invention. Those skilled in the art recognize that whatever the nature of the nucleic acid, the nucleic acid can be amplified using appropriate modifications to the present methods.

Due to the enormous amplification possible with the PCR process, small levels of DNA carryover from samples with high DNA levels, from positive control templates, or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, *Nature* 339:237–238 and Kwok, and Orrego, in Innis et al. eds., 1990 *PCR Protocols: A Guide to Methods anal Applications*, Academic Press, Inc., San Diego, Calif., which are incorporated herein by reference.

Enzymatic methods to reduce the problem of contamination of a PCR by the amplified nucleic acid from previous reactions are described in PCT Patent Publication No. WO 92/01814 and U.S. Pat. No. 5,035,996, both incorporated herein by reference. The methods allow the enzymatic degradation of any amplified DNA from previous reactions. PCR amplifications am carried out in the presence of dUTP instead of dTTP. The resulting double-stranded amplification product which incorporates uracil is subject to degradation by uracil-N-glycosylase (UNG), whereas normal thymine-containing DNA is not degraded by UNG. Amplification reaction mixtures are treated with UNG before amplification to degrade all uracil containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-inactivated environment and are not degraded.

Analysis of the amplified products may be achieved by a variety of means depending on the information desired. The nucleotide sequence of amplified products can be obtained using standard techniques, such as the protocol described by Innis et al., 1988, *Proc. Natl. Acad. Sci.* 85:9436–9440, incorporated herein by reference. The PCR amplification products can be sequenced directly (see Saiki et al., 1988, *Science* 239:487–491, incorporated herein by reference) or indirectly by first cloning the products and replicating them in an appropriate host cell.

Amplified nucleic acid sequences can be detected and purified by methods well known in the art (see Sambrook, et al., 1989, supra). Methods which separate molecules according to size, such as gel electrophoresis, can be used to purify the amplified nucleic acid. In particular, agarose and/or acrylamide gel electrophoresis are preferred means for analyzing amplified products (see Scharf et al., 1986, *Science* 233:1076–1078, incorporated herein by reference). For greater size resolution, either field inversion gel electrophoresis or low-percent (0.3%) agarose gel electrophoresis may be used, as described in the Examples.

Amplified products can be detected by direct visualization of the electrophoretically size fractionated product by, for example, staining with ethidium bromide. Alternatively, amplified products can be detected using oligonucleotide hybridization probes which are complementary to the target sequence. Under appropriate hybridization conditions, probes hybridize only to target nucleic acid sequences. The presence of hybrid duplexes, which can then be detected by various means, indicates the presence of amplified product. To facilitate the detection of hybrid duplexes formed between probes and target nucleic acid sequences, either the primers or the probes may be bound to additional molecules, such a detectable label or a molecule that enables the immobilization of the primer or probe. Labels incorporated into the probes to allow detection or immobilization should not affect the hybridization properties of the probes.

Probes can be labeled by incorporating a label detectable by spectroscopic, photochemical, biochemical, immunochemical, or chemical means. Useful labels include $^{32}P$, fluorescent dyes, electron-dense reagents, enzymes (as commonly used in ELISAs), biotin, or haptens and proteins for which antisera or monoclonal antibodies are available. Probes also can be bound to an additional compounds that are used to immobilize the probe on a solid support.

Labeled probes can be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for SSO probes is horseradish peroxidase (HRP). Methods for preparing and detecting probes containing this label are described in U.S. Pat. Nos. 4,914,210, and 4,962,029; both incorporated herein by reference. The use of such labeled probes is also described in U.S. Pat. No. 4,789,630; Saiki et al., 1988, *N. Eng. J. Med.* 319:537–541; and Bugawan et al., 1988, *Bio/Technology* 6:943–947, each of which is incorporated herein by reference. Useful chromogens for the detection of HRP labeled probes include red leuco dye and 3,3',5,5'-tetramethylbenzidine (TMB).

Examples of additional compounds incorporated into probes to allow immobilization of the probes include a long poly-dT "tail" that can be fixed to a nylon support by irradiation, a technique described in more detail in PCT Patent Publication No. 89/11548, incorporated herein by reference.

Suitable assay methods for detecting hybrids formed between probes and target nucleic acid sequences in a sample are known in the art (Sambrook et al., 1985, supra). Examples include the dot blot and reverse dot blot assay formats.

In a dot blot format, unlabeled amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

An alternate format is a "reverse" dot blot format, in which the amplified target DNA is labeled and the probes are immobilized on a solid support, such as a nylon membrane. The target DNA is typically labeled during amplification by the incorporation of labeled primers. The membrane-probe complex is incubated with the labeled sample under suitable hybridization conditions, unhybridized sample is removed by washing under suitably stringent conditions, and the filter is then monitored for the presence of bound target DNA.

Alternatively, the reverse dot blot assay may be carried out using a solid support having a plurality of probe hybridization sites or wells. For example, a microwell plate is particularly useful in large scale clinical applications of the present methods. A reverse dot blot assay utilizing a microwell plate is described in copending U.S. patent application Ser. No. 695,072, filed May 3, 1991, incorporated herein by reference, which is a CIP of U.S. Ser. No. 414,542, filed Nov. 20, 1991, now abandoned. Probes can be immobilized to a microwell plate either by passive binding or by first binding the probes to bovine serum albumin (BSA), which adheres to microwell plates.

Another suitable assay method system is described in U.S. Pat. No. 5,210,015, incorporated herein by reference, in which a labeled probe is added during the PCR amplification process. The probes are modified so as to prevent the probe from acting as a primer for DNA synthesis. Any probe which hybridizes to target DNA during each synthesis step is degraded by the 5'-to-3' exonuclease activity of the DNA polymerase. The degradation product from the probe is then detected. Thus, the presence of probe breakdown product indicates that hybridization between probe and target DNA occurred.

The present invention also relates to kits, multicontainer units comprising useful components for practicing the present method. A kit will contain a combination of preferred polymerase enzymes in the concentration ratios described herein. Additional components which may be contained in a useful kit include primers for PCR amplification and reagents for carrying out the PCR methods of the present invention.

The ability to amplify sequences of 10–40 kb has a number of applications in areas such as genome mapping, sequencing, and genetics. Small gaps in the genome maps that currently appear resistant to molecular cloning may be accessible by amplification of a sequence between known flanking sequences. The amplification of longer targets would also allow greater flexibility in choosing primers to avoid problematic sequences, such as that seen in the beta-globin gene system described below. Longer templates promise to speed the process of genomic sequencing as well, by increasing the distance covered with each sequencing step. From known expressed sequences, amplifications can be carried out spanning longer introns, and more complete genes sequences can be amplified at one time. Long PCR therefore complements technologies for rapid, long-range sequencing. PCR-based characterization and diagnosis of both homozygotes and heterozygote carriers of a number of medically important insertions and deletions of greater than 4 kb would also be possible.

The results presented here specifically demonstrate the potential application of these protocols to the characterization of cloned sequences. The J and cro gene primers, CF1018 (SEQ ID NO: 23) and CF1019 (SEQ ID NO: 24), described below should be useful for nearly all inserts cloned with lambda-based vectors, for amplifications from both plaques and isolated DNA. The PCR products are readily analyzed by restriction digests and should be suitable for sequencing. Cosmid inserts may also be amplifiable from colonies. Long PCR will facilitate molecular cloning by amplifying low-copy insert material, and facilitate assembly of larger recombinant constructions in PCR-based mutagenesis.

The examples of the present invention presented below are provided only for illustrative purposes and not to limit the scope of the invention.

EXAMPLE 1

Materials and Methods

Preferred protocols and reagents for the PCR amplification of long phage lambda and human beta-globin gene cluster sequences are described below. The results of amplifications using the following methods are described in the subsequent examples.

Target Nucleic Acid Sequences

Two template nucleic acid sequences were used for the design of the amplification primers described below, the sequence of the phage lambda genome (GenBank accession number M17233) and the sequence of the human beta-globin gene cluster (GenBank accession number J00 179). Phage lambda and human DNA were used in the amplifications described below.

Lambda DNA (1 ng/μl) was obtained from Perkin Elmer, Norwalk, Conn. Aliquots (~100 ng) of lambda DNA were thawed once, then stored at 4° C. Total genomic DNA from human placenta was obtained from Sigma Chemicals, St. Louis, Mo. All template DNA dilutions were made with 10 mM Tris.Cl (pH 8 at 25° C.), 0.1 mM EDTA.

A library of human genomic clones in lambda FIX II was obtained from Stratagene, La Jolla, Calif., and grown as recommended by the manufacturer, on Luria broth agar plates with top agarose. Randomly selected plaques were removed using siliconized Pasteur pipettes, and placed in 30 μl of 25 mM Tris.Cl (pH 8.3), 10 mM MgCl$_2$ and stored at 4° C. Aliquots of 1 μl were used for PCR.

Total genomic DNA from the KAS011 B-lymphoblastoid cell line was isolated using 0.1 mg/ml proteinase K and 0.5% SDS in 10 mM Tris.Cl (pH 8), 150 mM NaCl and 10 mM EDTA, overnight at 50° C. Following extraction with Tris-saturated phenol (pH 8), and ethanol-precipitation with NaOAc, the sample was treated with RNase A, then extracted with phenol-chloroform, and dialyzed against 10 mM Tris.Cl (pH 8), 1 mM EDTA.

Primers

A set of primers was designed to enable the PCR amplification of lambda genomic target sequences ranging in size from 1.5 to 42.2 kilobases in length. Upstream primers were designed to be used with each of the downstream primers, resulting in a series of target sequences increasing in length by 1 to 3 kilobase.

Each primer of the set was designed so as to have approximately the same optimal annealing temperature (~68° C.) by selecting primer sequences between 20 and 23 base pairs in length such that the hybrid duplex formed between the primer and target sequence would have an overall composition of 12 G-C pairings and 8–11 A-T pairings. Optimal annealing temperatures were estimated using the "$T_p$" algorithm of Wu et al., 1991, *DNA Cell Biol.* 10:233–238.

An additional pair of primers, the J and cro gene primers, were designed to enable amplification of nearly all inserts cloned with lambda-based vectors, from either plaques or isolated DNA, is shown in Table 2, below.

Similarly, primers were designed for the amplification of regions of the human beta-globin gene cluster. The primers were designed such that a fixed downstream primer could be used with a series of upstream primers to amplify targets of 7.5–22 kb. The primers amplify a target region extending upstream across the delta-globin gene and into the second intron of the A-gamma globin gene.

The nucleotide sequences of the primers used in the following examples are shown (5'-to-3') in Table 2, below. Melting temperatures ($T_m$) were calculated essentially as described in Wetmur, 1991, *Crit. Rev. Biochem. Mol. Biol.* 26:227–259, incorporated herein by reference. Melting temperature calculations were carried out assuming 2 dangling ends, 3.5 μg/ml (~0.5 μM) primer, 80 mM Na+, and 1.5 mM Mg$^{2+}$. Calculated melting temperatures ranged from 63°–70° C. The addition of 10% glycerol decreases the $T_m$ by 2.5° C. Primer nucleotide sequences were evaluated for potential secondary priming sites within the template DNA sequences and for inter- and intra-primer sequence complementation using the Oligo 4.0 software (National Biosciences, Plymouth, Minn.).

TABLE 2

| Amplification Primers | | | | |
|---|---|---|---|---|
| Primer | Seg ID No. | Sequence | Position | $T_m$ (°C.) |
| primers for phage lambda (GenBank accession no. M17233): | | | | |
| CF1001 | 1 | GGTGCTTTATGACTCTGCCGC | 304–324 | 67 |
| SC1011 | 2 | GCTGAAGTGGTGGAAACCGC | 506–525 | 67 |
| CF1005 | 3 | GCTCTTTCCGCTCTGCCATC | *1841–1860 | 66 |
| CF1007 | 4 | CGGCACTGGCAAGCAACTGA | *4921–4940 | 67 |
| CF1008 | 5 | CCTCAACCGGATCGAAGGCT | *6569–6588 | 67 |
| CF1010 | 6 | AGCGTGACGGTCACACCGTT | *9741–9760 | 70 |
| SC1012 | 7 | GACTCTGGCCATCTGCTCGT | *10600–10619 | 65 |
| CF1012 | 8 | GGACCTATCTGCCCGTTCGT | *12981–13000 | 67 |
| CF1013 | 9 | GCCACCAGTCATCCTCACGA | *14551–14570 | 65 |
| SC1000 | 10 | GCAGCGTGATTTCACGGTCG | *17025–17044 | 69 |
| SC1001 | 11 | GCTCACATAACGTCCACGCAG | *19259–19279 | 67 |
| SC1002 | 12 | GCCTCGCATATCAGGAAGCAC | *21359–21379 | 66 |
| SC1003 | 13 | GGGTGACGATGTGATTTCGCC | *23335–23355 | 67 |
| SC1008 | 14 | GGCATTCCTACGAGCAGATGGT | *26893–26914 | 66 |
| SC1009 | 15 | GGTCTGCCTGATGCTCCACT | *28536–28555 | 64 |

TABLE 2-continued

Amplification Primers

| Primer | Seg ID No. | Sequence | Position | $T_m$ (°C.) |
|---|---|---|---|---|
| SC1016 | 16 | GTCGGACTTGTGCAAGTTGCC | *30436–30456 | 67 |
| SC1017 | 17 | GCATGGATTCTGTCGACCCAC | *32741–32761 | 65 |
| SC1018 | 18 | GAGAACCACCGAGCCTGATG | *34413–34432 | 64 |
| SC1019 | 19 | AGCATTGGCCGTAAGTGCGATT | *35454–35475 | 69 |
| SC1021 | 20 | GGCCTTGTTGATCGCGCTTTGA | *38118–38139 | 70 |
| SC1022 | 21 | TGTCACGCCTGCCTGTTGCTT | *39505–39525 | 68 |
| SC1024 | 22 | GCGTTCCGCACGAGATACATG | *42730–42750 | 68 |
| Lambda vector primers, from the J and cro gene sites of phage lambda: | | | | |
| CF1018 | 23 | AGAAACAGGCGCTGGGCATC | 18872–18891 | 67 |
| CF1019 | 24 | CGGGAAGGGCTTTACCTCTTC | *38197–38217 | 66 |
| Primers for human beta-globin gene cluster (accession No. J00179): | | | | |
| RH1019 | 25 | CTGCTGAAAGAGATGCGGTGG | 54529–54549 | 65 |
| RH1020 | 26 | CTGCAGTCCCAGCTATTCAGG | 52152–52172 | 63 |
| RH1022 | 27 | CGAGTAAGAGACCATTGTGGCAG | 48528–48550 | 65 |
| RH1024 | 28 | TTGAGACGCATGAGACGTGCA | 44348–44369 | 67 |
| RH1025 | 29 | CCTCAGCCTCAGAATTTGGCAC | 42389–42410 | 65 |
| RH1026 | 30 | GAGGACTAACTGGGCTGAGACC | 40051–40072 | 65 |
| RH1016 | 31 | CAGCTCACTCAGTGTGGCAAAG | *62589–62610 | 64 |
| RH1053 | 32 | GCACTGGCTTAGGAGTTGGACT | *61986–62007 | 65 |

*Downstream primer complementary to position numbers listed.

Primers were synthesized using the cyanoethoxyphosphoramidite method (1 µM scale) on a 394 DNA Synthesizer (Applied Biosystems, Foster City, Calif.). The primers were deprotected and cleaved from the resin in 29% $NH_3$/ $H_2O$, then desalted with Sephadex G25 (NAP-10 columns from Pharmacia LKB, Piscataway, N.J.). The results of each synthesis were assessed by polyacrylamide gel electrophoresis. All primer stocks were made with 10 mM Tris.Cl (pH 8 at 25° C.), 0.1 mM EDTA.

Thermostable DNA Polymerases

Recombinant Tth DNA polymerase (rTth) was purchased from Perkin Elmer, Norwalk, Conn. The Tli DNA polymerase is described in U.S. Pat. No. 5,210,036, incorporated herein by reference. The Tli DNA polymerase (Vent$_R$®) and DNA polymerase from Pyrococcus species GB-D (Deep Vent$_R$®) were purchased from New England Biolabs, Beverly, Mass. The Tma DNA polymerase is described in European Pat. Publication No. WO 92/03556, incorporated herein by reference, and referred to therein as pTma12-3. A modified DNA polymerase from *Thermatoga maritima* is commercially available from Perkin Elmer, Norwalk, Conn. (UlTma™).

Dilutions (⅕ and 1/10) of the Vent$_R$® and Deep Vent$_R$® DNA polymerases preferably may be made in storage buffers as described by each manufacturer. In the Examples below, however, the Vent$_R$® dilution buffers used contained 1 mM EDTA and 0.05% Tween 20 (Sigma Chemicals, St. Louis, Mo.) instead of 0.1% Triton X-100. This modification had no effect on the amplification reactions. Vent$_R$® polymerase dilutions were made fresh weekly; Deep Vent$_R$® polymerase was diluted just before use. The polymerase can also be stored in the rTth DNA polymerase storage buffer supplied by the manufacturer (100 mM KCl, 20 mM Tris-HCl, pH 8.0, 0.1 mM EDTA, 1 mM DTT, 0.5% Tween® 20, 50% (v/v) glycerol).

Additional Buffer Components

Standard Tth polymerase buffer (5% (v/v) glycerol, 10 mM Tris.Cl (pH 8.3), 100 mM KCl, 0.75 mM EGTA, 0.05% Tween 20) for PCR was obtained from Perkin Elmer, Norwalk, Conn. Tricine buffer stocks (Sigma Chemicals, St. Louis, Mo.) at 1.0 M were adjusted to their final pH (at 25° C.) with KOH. Molecular biology grade dimethylsulfoxide (DMSO) and glycerol were from Sigma Chemicals, St. Louis, Mo., and J. T. Baker Chemicals, Phillipsburg, N.J., respectively. Potassium acetate (KOAc) was also obtained from J. T. Baker Chemicals. The contribution of glycerol (typically ≦1%) from enzyme storage buffers was not included in the glycerol concentrations given for any PCR buffer described herein.

PCR Methods

All lambda genomic DNA amplifications were performed in a GeneAmp® PCR System 9600 thermal cycler, using MicroAmp™ tubes with individual caps, all marketed by Perkin Elmer, Norwalk, Conn. Reaction volumes were either 50 or 100 µl. The concentration of each dNTP was 0.2 mM for all reactions, but other reaction components were varied as discussed in the text and listed in Table 1.

To minimize the amplification of non-specific sequences and the formation of primer-dimers, manual "hot-starts" were performed in which the $Mg^{2+}$ was withheld until the samples had been incubated in the thermal cycler at 75°–80° C. for ~90 seconds. The necessary $Mg^{2+}$ was then added from a 25 mM stock (at room temperature). Following the addition of $Mg^{2+}$, the samples were incubated for an additional 30–60 seconds, for a total of 4–7 minutes at 75°–80° C. prior to the first denaturation step. The total time includes the time required to add the $Mg^{2+}$, and therefore depends upon the total number of tubes. An alternate "hot-start" procedure is described in Example 6.

The thermal cycler was programmed to carry out a two-step temperature profile. Each amplification cycle consisted of denaturation at 94° C. for 10 seconds followed by annealing and extension at 68° C. for 5–20 minutes. A 15 second denaturation step can also be used. For annealing and extension times longer than 12–14 minutes, the autoextension feature of the thermal cycler was used to add 15–20 seconds per cycle, to a final ~16–22 minutes. Reactions were carried out for between 25 and 40 cycles, depending upon the starting target sequence copy number, the target length, and the reaction conditions. In most reactions, an initial 10 second incubation step at 94° C. and a final 10 minute incubation step at 72° C. were included.

The amplifications, described in the following examples, of human genomic inserts cloned into lambda FIX II and of regions of the human beta-globin gene cluster were carried out essentially as described above, but with the modifications detailed below. Specific conditions for the amplification of human genomic inserts cloned in lambda FIX II from plaque suspensions in 100 µl reaction volumes were as follows.

25 mM tricine (pH 8.7)
85 mM KOAc
12% (w/v) glycerol
0.2 mM each dNTP
0.4 µM each primer
1.75 U Tth polymerase
0.02 U Tli polymerase
1.15 mM Mg(OAc)$_2$ An 80° C. hot-start was used with a two-step thermal cycling profile, as described above. The annealing and extension step was initially 12 minutes at 68° C. and extended by 15 seconds per cycle for 32 cycles.

Specific conditions for the amplification of a region of the human beta-globin gene cluster from 37 ng of KAS011 DNA in 50 µl reaction volumes were as follows.

20 mM tricine (pH 8.7)
85 mM KOAc
10% (w/v) glycerol
2% (v/v) DMSO
0.2 mM each dNTP
0.2 µM each primer
0.9 U Tth polymerase
0.02 U Tli polymerase
1.1 mM Mg(OAc)$_2$ A 78° C. hot-start was used with a two-step thermal cycling profile, as described above. The annealing and extension step was initially 12 minutes at 68° C. for 12 cycles, then extended 15 seconds per cycle for 24 cycles.

Increased yields of amplified product may be obtained by the addition of up to 500 µg/ml of nonacetylated BSA to the amplification reaction.

Analysis of PCR products

Typically, 5–8 µl from each PCR amplification were analyzed on standard horizontal gels consisting of 0.6% (w/v) SeaKem GTG agarose (FMC BioProducts, Rockland, Me.) in 1X TBE (89 mM Tris base, 89 mM boric acid, 1 µM to 2 mM EDTA) or 1X TAE (40 mM Tris-acetate, 2 mM EDTA, pH 8–8.5) with 0.5 µg/ml ethidium bromide, at about 4–6 V/cm for 1.5–2 hours. For greater size resolution, two alterative were used: field inversion gel electrophoresis and 0.3% agarose gel electrophoresis.

Field inversion gel electrophoresis (FIGE) was performed using a Hoefer system (SuperSub gel apparatus, Switchback pulse controller, and power supply, all from Hoefer, San Francisco, Calif.) with a cooling unit (2219 Multitemp II from Pharmacia LKB). Between 3 and 7 µl from each PCR amplification were analyzed on FIGE gels of 0.95% agarose in 0.5×TBE (at 1 µM EDTA). The FIGE gels were prerun for 15 minutes at 110 V, then run for 22–25 hours at 140–145 V, with pulse times of 0.65–1.95 or 0.75–2 seconds (forward-:reverse=2.8:1 or 3:1). Run temperatures were estimated at 12°–15° C.

Alternatively, load 2–5 µl on 0.3% Chromosomal Grade agarose (Bio-Rad, Richmond, Calif.) or Seakem GTG or Gold (FMC BioProducts, Rockland, Me.) in 1X TAE. Cool the gel to 4° C. before removing the comb. Load 5–8 µl of sample and run in 1X TAE with 0.5% ethidium bromide at 100 V for 2 minutes, then either at 1.5 V/cm for 6 hours or at 0.7 V/cm for 16 hours.

The size of the amplified products was determined by comparison with molecular weight markers run on each gel in addition to the sample. Molecular weight markers used were lambda/HindlII from either New England Biolabs or Gibco BRL, lambda/mono cut mix from New England Biolabs, and 1-kb ladder from Gibco BRL.

For restriction analyses, aliquots (10–16 µl) of PCR amplification product from lambda DNA amplifications were digested with BclI, BssHII, and MluI (New England Biolabs); or BamHI, EcoRI, and HindlII (Gibco BRL), using the manufacturer's buffers, prior to electrophoresis. Digestions were carried out for 2.5–3 hours in 30–36 µl reactions. Samples were analyzed using 0.6–8% agarose gels. Aliquots of plaque PCR samples (10–30 µl aliquots) were digested with NotI (Stratagene) overnight in 40 µl reactions.

EXAMPLE 2

Amplification of Phage Lambda Genomic Sequences

Amplifications were carried out using target sequences from high copy ($10^7$–$10^8$ copies of target) phage lambda DNA samples as described in Example 1, above. Targets of 1.5 to 42.2 kb were defined within this ~50-kb sequence (GenBank M17233) by the various pairings of the primers listed in Table 2, above.

Amplified product was analyzed by field inversion gel electrophoresis (FIGE) and visualized with ethidium bromide staining. Total yields (per 50 µl), as estimated by comparison with a lambda/HindlII molecular weight marker, were estimated at between 0.7–1 µg of 22.8 kb product and 0.2–0.3 µg of 39-kb product. A 42.2 kb target, amplified using primers SC1011 (SEQ ID NO: 2) and SC1024 (SEQ ID NO: 22), was amplified with lower yields.

EXAMPLE 3

Amplification of Lambda Clones From Plaques

One important use for the methods of the present invention is the amplification of inserts from lambda clones without prior, labor and time intensive DNA isolations. To demonstrate the utility of the present methods to the amplification of such inserts, primers CF1018 (SEQ ID NO: 23) and CF1019 (SEQ ID NO: 24) were designed from sequences within the J and cro genes of lambda (see Table 2).

Amplifications were carried out as described in Example 1 using randomly selected plaques from the human genomic library in lambda FIX II described in Example 1. Amplification products were analyzed by gel electrophoresis following digestion with NotI to separate the insert from flanking vector sequences. The presence of both vector fragments confirms that the entire insert was amplified.

The size of the amplified inserts ranged from less than 10 kb to greater than 20 kb. The manufacturer estimates that insert sizes of 9–23 kb are accommodated by this lambda vector. Inserts were sized by their mobility relative to molecular weight markers in FIGE gels.

EXAMPLE 4

Amplifications of Human Genomic Targets

The human beta-globin gene cluster was chosen as a model for genomic targets that are likely to contain repetitive sequences and homologous sites elsewhere in the genome. Primers designed for the human beta-globin gene cluster are shown in Table 2, above. A fixed downstream primer was paired with a series of upstream primers that amplify a region extending upstream across the delta-globin gene and into the second intron of the A-gamma globin gene. Targets of 13.5, 17.7, 19.6, and 22 kb were amplified from 37 ng (~$10^4$ copies) of total human genomic DNA as described in Example 1. Aliquots of 12.5 µl of the amplified products were loaded on FIGE gels. A lambda/HindlII molecular weight marker was used for comparison.

For comparison, targets of 16.5, 18.8, 20.8, and 22.8 kb were amplified from 0.05 pg. (~$10^3$ copies) or 0.5 pg (~$10^4$ copies) phage lambda DNA in a background of ~3.7 ng or 37 ng, respectively, human placental genomic DNA, under the same conditions. By also amplifying from a low input target number a target previously amplified from a high input target number, the effects attributable to a decrease in input target copy number can be separated from the effects attributable to a difference in target sequence.

Target sequences up to 22 kb in length of the beta-globin gene cluster were amplified. The beta-globin targets were amplified less efficiently than lambda sequences of similar length that were at a single-copy level in a background of human placental DNA, either at the same overall concentration as the globin target or at a 10fold lower concentration. These efficiency differences may reflect the relative sequence complexities, even though the lambda target was also in a human genomic background. The increased likelihood that long targets will contain sites sufficiently homologous to act as secondary primer annealing sites, and the presence of repetitive sequences in human genomic sequences, may explain why lambda targets were more efficiently amplified then beta-globin gene targets of comparable length.

The problem of secondary priming sites also affected the choice of suitable primers for the amplification of beta-globin gene targets. Downstream primer RH 1053 (SEQ ID NO: 32), which hybridizes 5' to the beta-globin gene, was chosen because RH1016 (SEQ ID NO: 31), which hybridizes within exon 2 of the beta-globin gene, also hybridizes to a secondary sites within targets longer than 14 kb, resulting in multiple products. The upstream primer RH1020 (SEQ ID NO: 26) resulted in multiple secondary products, as did the use of two other primers (not shown) within 100 bases of RH1020 (SEQ ID NO: 26). All three lie within an Alu repeat sequence.

Results from amplifications of sequences up to 16 kb in length from the human neurofibromatosis-1 gene also suggested that methods to insure primer specificity are crucial to efficient PCR amplification of long target sequences.

EXAMPLE 5

DNA Polymerase Combinations

To access the relative efficiency of various DNA polymerase combinations, amplification reactions were carried out essentially as described in Example 1, above, using primers which amplify target sequences 22.8, 26.4, 29.9, and 33.9 kb in length. The DNA polymerase combinations compared were as follows:

2.5 U rTth DNA polymerase+0.02 U Vent$_R$® DNA Polymerase 2.5 U rTth DNA polymerase+0.06 U Deep Vent$_R$® DNA Polymerase 3.15 U rTth DNA polymerase+0.5 U Tma DNA Polymerase All reactions were carried out in 50 µl, with $10^7$ copies of lambda DNA, 0.45 µM each primer and 1.0–1.1 mM Mg(OAc)$_2$. Amplification reactions using the following specific conditions.

Reactions using either rTth and Vent$_R$® or rTth and Deep Vent$_R$® DNA polymerases were carried out in 20 mM tricine (pH 8.7), 85 mM KOAc, 10% glycerol, and 3% DMSO. Reactions using rTth and Tma DNA polymerases were carried out in 20 mM tricine (pH 8.7), 85 mM KOAc, 10% glycerol, and 2.5% DMSO.

The temperature cycling profile was essentially as described in Example 1, above. An initial 13-minute extension time was used for the first 9 cycles. The extension time was then increased to 13.5 minutes and increased 20 seconds in each subsequent cycle for 18 cycles. Seven µl aliquots of each reaction were loaded on a standard agarose gel along with 150 ng of the lambda/HindlII molecular weight marker.

All templates (to 33.9 kb) were amplified using combinations of rTth DNA polymerase with Vent$_R$®, Deep Vent$_R$®, and Tma DNA polymerases. The combination of 2.5 U rTth DNA polymerase and 0.02 U Vent$_R$® DNA Polymerase amplified all targets with the greatest efficiency.

EXAMPLE 6

PCR Amplification Kit

The reagents of the invention are suitable for inclusion in a kit for carrying out the PCR amplification of long target sequences. A kit contains at least a DNA polymerases mixture as described herein. Additional, optional, components include additional reagents and reaction containers used in the reactions as described below.

A preferred combination of DNA polymerases useful for amplifying both high copy and low copy targets consists of rTth and Vent$_R$® DNA polymerases in a ratio of 2 units of rTth DNA polymerase to 0.08 units of Vent$_R$® DNA polymerase. Although, as shown below, the preferred polymerase concentration for the amplification of high copy targets is twice the preferred concentration for the amplification of low copy targets, the ratio of primary to secondary polymerases is the same.

A reaction buffer suitable for inclusion in a kit consists of tricine, KOAc, glycerol, and DMSO in about the following concentrations:

25 mM tricine (pH 8.7)

80 mM KOAc

10% (w/v) glycerol 2.25% (v/v) DMSO

The term "about" is meant to encompass a standard plus or minus 10% manufacturing tolerance. For convenience, the reaction buffer may be stored at a higher concentration and diluted before using.

Amplifications are carried out using the preferred kit components essentially as described above, but using the preferred reaction conditions described below. These reagents and conditions have been used extensively and have been found to provide reliable amplification of long target sequences.

Preferred conditions for the amplification of low copy (e.g. human genomic) targets ($2.0 \times 10^4$ copies) in 100 µl reaction volumes are as follows.

25 mM tricine (pH 8.7)

80 mM KOAc

10% (w/v) glycerol
2.25% (v/v) DMSO
0.2 mM each dNTP
0.2 µM each primer
2 U rTth polymerase
0.08 U Vent$_R$® polymerase
1.1 mM Mg(OAc)$_2$ Preferred cycling parameters for the amplification of low copy targets (>10 kb) are as follows:

| Denaturation | 94° C. | 1 minute |
|---|---|---|
| 20 Cycles | 94° C. | 15 seconds |
| | 68° C. | 12 minutes |
| 17 Cycles | 94° C. | 15 seconds |
| | 68° C. | 12 minutes with 15 second autoextend |
| Final Extend | 72° C. | 10 minutes |
| Hold | 4° C. | indefinite |

Preferred conditions for the amplification of high copy (e.g. cloned DNA) targets ($2.0 \times 10^7$ copies) in 100 µl reaction volumes are as follows.

25 mM tricine (pH 8.7)
80 mM KOAc
10% (w/v) glycerol
2.25% (v/v) DMSO
0.2 mM each dNTP
0.4 µM each primer
4 U rTth polymerase
0.16 U Vent$_R$® polymerase
1.1 mM Mg(OAc)$_2$ Preferred cycling parameters for the amplification of high copy targets (<10 kb) are as follows:

| Denaturation | 94° C. | 1 minute |
|---|---|---|
| 16 Cycles | 94° C. | 15 seconds |
| | 68° C. | 10 minutes |
| 12 Cycles | 94° C. | 15 seconds |
| | 68° C. | 10 minutes with 15 second autoextend |
| Final Extend | 72° C. | 10 minutes |
| Hold | 4° C. | indefinite |

A "hot-start" is achieved by separating reagents within the reaction tubes using Ampliwax™ PCR Gem 100 wax beads, developed and manufactured by Hoffmann-La Roche and marketed by Perkin Elmer, Norwalk, Conn. A 40 µl bottom reagent layer containing buffer (tricine, KOAc, glycerol, and DMSO), Mg(OAc)$_2$, and the dNTP's is added to the reaction tube. A wax layer is established over the bottom layer by adding an Ampliwax™ PCR Gem 100 and incubating in a thermal cycler first at 80° C. for 5 minutes, and then at 25° C. for 5 minutes. A 60 µl top reagent layer is then added containing buffer, the DNA polymerase mixture, the primers, and the target DNA.

Samples are analyzed as described above on a 0.6% Agarose gel in 1X TAE and 0.5 µg/ml EtBr for 1.5 hours at 7 V/cm.

---

We claim:

1. A DNA polymerase composition for the polymerase chain reaction amplification of long nucleic acid sequences consisting of a combination of a first DNA polymerase and a lesser quantity, measured in units of polymerase activity, of a second DNA polymerase, wherein said first DNA polymerase is *Thermus thermophilus* DNA polymerase, and wherein said second DNA polymerase is selected from the group of DNA polymerases consisting of *Thermococcus litoralis* DNA polymerase, Pyrococcus species GB-D DNA polymerase, and *Thermotoga maritima* DNA polymerase.

2. The DNA polymerase composition of claim 1, wherein said second DNA polymerase is *Thermococcus litoralis* DNA polymerase.

3. The DNA polymerase composition of claim 2, wherein said DNA polymerase composition consists of about 0.8–2.5 units of first DNA polymerase for each 0.015–0.15 units of second DNA polymerase.

4. The DNA polymerase composition of claim 2, wherein said DNA polymerase composition consists of about 2 units of first DNA polymerase for each 0.08 units of second DNA polymerase.

5. A kit comprising the DNA polymerase composition of claim 4.

6. A kit of claim 6 further comprising a reaction buffer for the polymerase chain reaction amplification of long nucleic acid sequences comprising about 25 mM tricine, 80 mM KOAc, 10% (w/v) glycerol, and 2.25% (v/v) DMSO.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGTGCTTTAT GACTCTGCCG C      21

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCTGAAGTGG TGGAAACCGC      20

( 2 ) INFORMATION FOR SEQ ID NO:3:

( i ) SEQUENCE CHARACTERISTICS:
        ( A ) LENGTH: 20 base pairs
        ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:3:

GCTCTTTCCG CTCTGCCATC 20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGGCACTGGC AAGCAACTGA 20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCTCAACCGG ATCGAAGGCT 20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGCGTGACGG TCACACCGTT 20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GACTCTGGCC ATCTGCTCGT 20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:8:

GGACCTATCT GCCCGTTCGT 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCCACCAGTC ATCCTCACGA 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GCAGCGTGAT TTCACGGTCG 20

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GCTCACATAA CGTCCACGCA G 21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GCCTCGCATA TCAGGAAGCA C 21

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GGGTGACGAT GTGATTTCGC C 21

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GGCATTCCTA CGAGCAGATG GT                                                        22

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGTCTGCCTG ATGCTCCACT                                                          20

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GTCGGACTTG TGCAAGTTGC C                                                       21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GCATGGATTC TGTCGACCCA C                                                       21

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GAGAACCACC GAGCCTGATG                                                          20

( 2 ) INFORMATION FOR SEQ ID NO:19:

( i ) SEQUENCE CHARACTERISTICS:
        ( A ) LENGTH: 22 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:19:

AGCATTGGCC GTAAGTGCGA TT                                    22

(2) INFORMATION FOR SEQ ID NO:20:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:20:

GGCCTTGTTG ATCGCGCTTT GA                                    22

(2) INFORMATION FOR SEQ ID NO:21:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:21:

TGTCACGCCT GCCTGTTGCT T                                     21

(2) INFORMATION FOR SEQ ID NO:22:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:22:

GCGTTCCGCA CGAGATACAT G                                     21

(2) INFORMATION FOR SEQ ID NO:23:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:23:

AGAAACAGGC GCTGGGCATC                                       20

(2) INFORMATION FOR SEQ ID NO:24:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: DNA (genomic)

( x i ) SEQUENCE DESCRIPTION: SEQ ID NO:24:

CGGGAAGGGC TTTACCTCTT C 21

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CTGCTGAAAG AGATGCGGTG G 21

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CTGCAGTCCC AGCTATTCAG G 21

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CGAGTAAGAG ACCATTGTGG CAG 23

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TTGAGACGCA TGAGACGTGC AG 22

( 2 ) INFORMATION FOR SEQ ID NO:29:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

CCTCAGCCTC AGAATTTGGC AC 22

( 2 ) INFORMATION FOR SEQ ID NO:30:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GAGGACTAAC TGGGCTGAGA CC          22

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CAGCTCACTC AGTGTGGCAA AG          22

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

GCACTGGCTT AGGAGTTGGA CT          22